United States Patent [19]
Gray

[11] Patent Number: 5,629,337
[45] Date of Patent: May 13, 1997

[54] METHODS FOR TREATING ASTHMA USING OPTICALLY PURE (−)-ZILEUTON

[75] Inventor: Nancy M. Gray, Marlboro, Mass.

[73] Assignee: Sepracor, Inc., Marlborough, Mass.

[21] Appl. No.: 369,254

[22] Filed: Jan. 5, 1995

Related U.S. Application Data

[63] Continuation of Ser. No. 59,632, May 10, 1993, abandoned.

[51] Int. Cl.$^6$ .................................................. A61K 31/38
[52] U.S. Cl. ............................................................... 514/443
[58] Field of Search ............................................... 514/443

[56] References Cited

U.S. PATENT DOCUMENTS 4,873,259  10/1989  Summers, Jr. et al. ................. 514/443

FOREIGN PATENT DOCUMENTS 0279263  2/1988  European Pat. Off. .
WO92/03130  8/1991  WIPO .

OTHER PUBLICATIONS

Bell et al. "The Discovery and Development of Zileuton: An Orally Active 5–Lipoxygenase Inhibitor" *Int. J. Immunopharmac.* 14, 505–510 (1992).
Carter et al. "5–Lipoxygenase Inhibitory Activity of Zileuton" *J. Phar. and Exp. Ther.* 256, 929–937 (1990).
Hsiao et al. "Synthesis of Chiral Zileuton, A Potent and Selective Inhibitor of 5–Lipoxygenase" *Tet. Ltrs.* 33, 2629–2632 (1992).
Sweeny et al. "Enantiomeric Activation of Glucronidation in Dog Hepatic Microsomes" *J. Biol. Chem.* 267, 13171–13174 (1992).
Siris et al. "Effect of Zileuton (A–64077) on the 5–Lipoxygenase activity of human whole blood ex vivo" *Agents and Actions*, 34, 117–120 (1991).
Weinblatt et al. "Zileuton, A 5–Lipoxygenase Inhibitor in Rheumatoid Arthritis" *J. Rheum.* 19, 1537–1541 (1992).
Laursen et al. "Selective 5–lipoxygenase inhibition in ulcerative colitis" *Lancet* 335, 683–685 (1990).
Israel et al. "The Effects of a 5–Lipoxygenase Inhibitor on Asthma Induced By Cold, Dry Air" *N. Eng. J. Med.* 323, 1740–1744 (1990).
Collawn et al. "Phase II Study of the Safety and Efficacy of a 5–Lipoxygenase Inhibitor in Patients with Ulcerative Colitis" *Amn. J. Gastro.* 87, 342–346 (1992).
Knapp "Reduced Allergen–Induced Nasal Congestion and Leukotriene Synthesis With An Orally Active 5–Lipoxygenase Inhibitor" *N. Eng. J. Med.* 323, 1745–1748 (1990).

*Primary Examiner*—Marianne M. Cintins
*Assistant Examiner*—William R. A. Jarvis
*Attorney, Agent, or Firm*—Heslin & Rothenberg, P.C.

[57] ABSTRACT

Methods are disclosed utilizing optically pure (−)-zileuton for the treatment of asthma in humans while substantially reducing the concomitant liability of adverse effects associated with the racemic mixture of zileuton.

8 Claims, No Drawings

METHODS FOR TREATING ASTHMA USING OPTICALLY PURE (−)-ZILEUTON

This application is a continuation of application Ser. No. 08/059,632, filed May 10, 1993 now abandoned.

BACKGROUND OF THE INVENTION

This invention relates to novel compositions of matter containing optically pure (−)-zileuton. These compositions possess potent activity in treating asthma, ulcerative colitis, rheumatoid arthritis, psoriasis, allergic rhinitis and other diseases including those that would benefit from a selective inhibition of 5-lipoxygenase. By virtue of the antioxidant activity of (−)-zileuton, the compositions are also useful for treating atherosclerosis. Optically pure (−)-zileuton provides this treatment while substantially reducing adverse effects including, but not limited to, headache, nausea, fatigue, diarrhea, dyspepsia, chills, dizziness and paresthesia, which are associated with the administration of the racemic mixture of zileuton. Also disclosed are methods for treating the above described conditions in a human while substantially reducing the adverse effects that are associated with the racemic mixture of zileuton by administering the (−) isomer of zileuton to said human.

The active compound of these compositions and methods is an optical isomer of zileuton. The preparation of racemic zileuton is described in U.S. Pat. No. 4,873,259 and European application 279263. The medicinal chemistry of zileuton is described in Bell et al. [Intl. J. Imm. Pharmacol. 14, 505–510 (1992)], Abraham et al. [Europ. J. Pharmacol. 217, 119–126 (1992)], Carter et al. [J. Pharm. Exp. Ther. 256, 929–937 (1991)], and Sirois et al. [Agents and Actions 34, 117–120 (1991)]. Chemically, the active compound is the (−) isomer of N-(1-benzo[b]thien-2-ylethyl)-N-hydroxyurea, hereinafter referred to as zileuton. It appears to have the S absolute stereochemistry as shown in formula I:

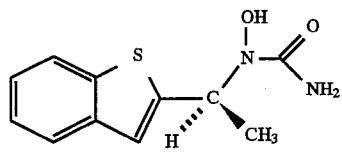

(−)-Zileuton, which is the subject of the present invention, is not presently commercially available. All of the medicinal chemistry that has been reported has utilized the racemic mixture, which is available for research purposes only.

Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. There is no correlation between nomenclature for the absolute stereochemistry and for the rotation of an enantiomer. Thus, D-lactic acid is the same as (−) lactic acid, and L-lactic acid is (+). For a given chemical structure, these chiral compounds exist as a pair of enantiomers which are identical except that they are non-superimposable mirror images of one another. A specific stereoisomer may also be referred to as an enantiomer, and a mixture of such isomers is often called an enantiomeric or racemic mixture.

Stereochemical purity is of importance in the field of pharmaceuticals, where 12 of the 20 most prescribed drugs exhibit chirality. A case in point is provided by the L-form of the beta-adrenergic blocking agent, propranolol, which is known to be 100 times more potent than the D-enantiomer.

Furthermore, optical purity is important since certain isomers may actually be deleterious rather than simply inert. For example, it has been suggested that the D-enantiomer of thalidomide was a safe and effective sedative when prescribed for the control of morning sickness during pregnancy, while the corresponding L-enantiomer has been believed to be a potent teratogen.

Notwithstanding the paper by Sweeny and Nellans (below), neither the separation of racemic zileuton nor the synthesis of (−) zileuton has been described. However, the enantioselective synthesis of the (+)-isomer from L-(+)-lactic acid has been described by Hsiao and Kolasa [Tetra. Letters 33, 2629–2632 (1992)]. The selective glucuronidation of S-(−)-zileuton and the enhancement of that reaction by the R-isomer in dog liver microsomes has been reported by Sweeney and Nellans [J. Biol. Chem. 267, 13171–13174 (1992)]. No medicinal chemistry of the individual enantiomers is reported.

Racemic zileuton has been in clinical trials in the United States for use in rheumatoid arthritis [Weinblatt et al., J. Rheumatology 19, 1537–1541 (1992)], for asthma [Israel et al., N. Eng. J. Med. 323, 1740–1744 (1990)], for ulcerative colitis [Laursen et al., Lancet 335, 683–6835 (1990)] and for allergen induced nasal congestion [Knapp, N. Eng. J. Med. 323, 1745–1748 (1990)]. The results of the preliminary clinical studies indicate that racemic zileuton may be clinically useful in all of these disease states because of its suppression of leukotriene production.

The leukotrienes are a family of highly potent biological substances derived from arachidonic acid and are believed to be involved in mediating a spectrum of human disorders. Considerable evidence suggests that the leukotrienes contribute to the asthmatic response and that they are mediators of other inflammatory diseases (see Carter, et al. op. cit.). Because several 5-lipoxygenase metabolites are likely to be generated at sites undergoing pathological reactions, and because these metabolites then act in concert to produce the clinical condition, it is thought advantageous to inhibit the formation of the constellation of metabolites to achieve therapeutic benefit. Since 5-lipoxygenase is the first enzymatic step in the conversion of arachidonic acid to leukotrienes, its inhibition should decrease the production of all of the pro-inflammatory metabolites. Racemic zileuton has been found to be a very selective inhibitor of mammalian 5-lipoxygenase with little inhibitory effect on human platelet 12-lipoxygenase, soybean 15-lipoxygenase or sheep seminal vesicle cyclooxygenase. In human volunteers doses of 800 mg p.o. twice per day for four weeks resulted in 75 to 85% decreases in $LTB_4$ and statistically significant improvement in symptoms of rheumatoid arthritis. (Weinblatt op. cit.) One hundred percent of the patients receiving racemic zileuton reported an adverse event during the four week trial. The adverse events included headaches, nausea, fatigue, diarrhea, dyspepsia, chills, dizziness, paresthesia and infections.

In pre-clinical trials, racemic zileuton was absorbed rapidly in all of the species tested with $T_{max}$ values ranging from 15 minutes to one hour. The elimination half life for the racemic compound, estimated from oral studies, varied markedly among species from 20 minutes in monkeys to 7 hours in dogs. While clinical trials have so far been limited to rheumatoid arthritis, asthma, ulcerative colitis and allergen induced nasal congestion, it is believed that as a result of its 5-lipoxygenase inhibitory activity racemic zileuton may also be useful to treat gout, psoriasis, adult respiratory distress syndrome, Crohn's disease, endotoxin shock, inflammatory bowel disease and ischemia induced by myocardial or cerebral injury.

Thus it would be particularly desirable to find a compound with the advantages of the racemic mixture of zileuton which would not have the aforementioned disadvantages.

SUMMARY OF THE INVENTION

It has now been discovered that the optically pure (−) isomer of zileuton is an effective agent for treating asthma, ulcerative colitis, rheumatoid arthritis, psoriasis, allergic rhinitis and other disorders including those that would benefit from an inhibitory action on 5-lipoxygenase. It is also useful for treating atherosclerosis. The optically pure (−) isomer of zileuton provides this effective treatment while substantially reducing the adverse effects of racemic zileuton including, but not limited to, headache, nausea, fatigue, diarrhea, dyspepsia, chills, dizziness and paresthesia. The present invention also includes methods for treating the above described conditions in a human while substantially reducing the adverse effects that are associated with the racemic mixture of zileuton by administering the optically pure (−) isomer.

DETAILED DESCRIPTION OF THE INVENTION

The present invention encompasses a method of treating asthma, which comprises administering to a human in need of such therapy, an amount of (−)-zileuton, or a pharmaceutically acceptable salt thereof, substantially free of its (+) stereoisomer, said amount being sufficient to alleviate the symptoms of asthma. The method substantially reduces the concomitant liability of adverse effects associated with the administration of the racemic compound by providing an amount which is insufficient to cause the adverse effects associated with the racemic mixture of zileuton.

The present invention also encompasses a composition for the treatment of a human afflicted with asthma, which comprises an amount of (−)-zileuton, or a pharmaceutically acceptable salt thereof, substantially free of its (+) stereoisomer, said amount being sufficient to alleviate said asthma. Preferably the amount is insufficient to cause the adverse effects associated with racemic zileuton.

The present invention further encompasses a method of treating rheumatoid arthritis in a human, which comprises administering to a human in need of such therapy, an amount of (−)-zileuton, or a pharmaceutically acceptable salt thereof, substantially free of its (+) stereoisomer, sufficient to alleviate the symptoms of rheumatoid arthritis. The method substantially reduces the concomitant liability of adverse effects associated with the administration of racemic zileuton by providing an amount which is insufficient to cause adverse effects associated with the administration of racemic zileuton.

In addition, the present invention encompasses a composition for the treatment of a human having rheumatoid arthritis, which comprises an amount of (−)-zileuton, or a pharmaceutically acceptable salt thereof, substantially free of its (+) isomer, said amount being sufficient to alleviate or palliate said disorder. Preferably the amount is insufficient to cause adverse effects associated with the administration of racemic zileuton.

The present invention further encompasses a method of treating ulcerative colitis in a human, which comprises administering to a human in need of such therapy, an amount of (−)-zileuton, or a pharmaceutically acceptable salt thereof, substantially free of its (+) stereoisomer, sufficient to alleviate the symptoms of ulcerative colitis. The method substantially reduces the concomitant liability of adverse effects associated with the administration of racemic zileuton by providing an amount which is insufficient to cause adverse effects associated with the administration of racemic zileuton.

In addition, the present invention encompasses a composition for the treatment of a human having ulcerative colitis, which comprises an amount of (−)-zileuton, or a pharmaceutically acceptable salt thereof, substantially free of its (+) isomer, said amount being sufficient to alleviate or palliate said disorder. Preferably the amount is insufficient to cause adverse effects associated with the administration of racemic zileuton.

A further aspect of the present invention includes a method of treating a condition caused by or contributed to by elevated levels of leukotrienes in a human, which comprises administering to a human in need of such therapy, an amount of (−)-zileuton, or a pharmaceutically acceptable salt thereof, substantially free of its (+) stereoisomer, sufficient to reduce said elevated levels of leukotrienes. The method substantially reduces the concomitant liability of adverse effects associated with the administration of racemic zileuton by providing an amount which is insufficient to cause adverse effects associated with the administration of racemic zileuton. Conditions associated with elevated leukotriene levels in humans may include, but are not limited to, allergic rhinitis, psoriasis, gout, Crohn's disease, adult respiratory distress syndrome (ARDS), endotoxin shock, inflammatory bowel disease and ischemia from myocardial or cerebral injury.

In addition, the invention encompasses a composition for the treatment of a condition caused by or contributed to by elevated leukotriene levels in a human which comprises an amount of (−)-zileuton or a pharmaceutically acceptable salt thereof, substantially free of its (+) stereoisomer, the amount being sufficient to alleviate the condition. Preferably the amount is insufficient to cause adverse effects associated with the administration of racemic zileuton.

The present invention further encompasses a method of treating atherosclerosis in a human, which comprises administering to a human in need of such therapy, an amount of (−)-zileuton, or a pharmaceutically acceptable salt thereof, substantially free of its (+) stereoisomer, sufficient to reduce atherosclerotic plaque. The method substantially reduces the concomitant liability of adverse effects associated with the administration of racemic zileuton by providing an amount which is insufficient to cause adverse effects associated with the administration of racemic zileuton.

In addition, the present invention encompasses a composition for the treatment of a human having atherosclerosis, which comprises an amount of (−)-zileuton, or a pharmaceutically acceptable salt thereof, substantially free of its (+) isomer, said amount being sufficient to reduce atherosclerotic plaque. Preferably the amount is insufficient to cause adverse effects associated with the administration of racemic zileuton.

The racemic mixture of zileuton (i.e., a 1:1 racemic mixture of the two enantiomers) exhibits antiasthmatic and antiinflammatory activity through its selective and potent 5-lipoxygenase inhibition, thus providing therapy and a reduction of symptoms in a variety of conditions and disorders related to elevated leukotriene levels; it also exhibits antiatherosclerotic activity by virtue of its inhibition of oxidative modification of lipids. However, this racemic mixture, while offering the expectation of efficacy, causes adverse effects. Utilizing the optically pure or substantially optically pure isomer of (−)-zileuton results in enhanced efficacy, diminished adverse effects and, accordingly, an improved therapeutic index. It is therefore more desirable to use the (−) isomer of zileuton than to administer the racemic mixture.

The term "adverse effects" includes, but is not limited to, headache, nausea, fatigue, diarrhea, dyspepsia, chills, dizziness and paresthesia.

The term "substantially free of its (+) stereoisomer" as used herein means that the compositions contain at least 90% by weight of (−)-zileuton and 10% by weight or less of (+) zileuton. In a more preferred embodiment the term "substantially free of the (+) isomer" means that the composition contains at least 99% by weight of (−)-zileuton, and 1% or less of (+) zileuton. In the most preferred embodiment, the term "substantially free of its (+) stereoisomer" as used herein means that the composition contains greater than 99% by weight of (−)-zileuton. These percentages are based upon the total amount of zileuton in the composition. The terms "substantially optically pure (−) isomer of zileuton" or "substantially optically pure (−)-zileuton" and "optically pure (−) isomer of zileuton" or "optically pure (−)-zileuton" are also encompassed by the above-described amounts.

The term "treating asthma" as used herein means treating, alleviating or palliating such conditions, and thus providing relief from the symptoms of shortness of breath, bronchoconstriction, mucus hypersecretion and slowed mucociliary clearance.

The term "treating rheumatoid arthritis" as used herein means treating, alleviating or palliating such conditions and thus providing relief from the symptoms of painful or tender joints, swollen joints and loss of mobility.

The term "treating ulcerative colitis" as used herein means treating, alleviating or palliating such conditions and thus providing relief from the symptoms of diarrhea, loose stools, rectal bleeding, abdominal and rectal pain and urgency.

The term "treating a condition caused, or contributed to, by elevated levels of leukotrienes" as used herein means treating, alleviating or palliating such disorders associated with elevated leukotriene levels thus providing relief from the symptoms of the aforementioned conditions. Among such conditions are allergic rhinitis, psoriasis, gout, Crohn's disease, adult respiratory distress syndrome, endotoxin shock, inflammatory bowel disease and ischemia from myocardial or cerebral injury.

The term "treating or preventing atherosclerosis" as used herein means reducing atherosclerotic plaque in a patient thus providing decreased likelihood of stroke, myocardial infarct and related cardiovascular obstructive events.

The chemical synthesis of the racemic mixture of zileuton can be performed by the method described in U.S. Pat. No. 4,873,259 cited above. The (−) isomer of zileuton may be obtained by resolution of the enantiomers of zileuton or of precursors thereto using conventional means such as alkylation with a chiral halide that can be cleaved after resolution. For example, German application 4,035,455 (Kohl et al.) discloses a method adaptable to resolving a racemic alcohol by forming an alkoxymethylether with fenchyl chloromethyl ether. Other standard methods of resolution known to those skilled in the art including, but not limited to, simple crystallization and chromatographic resolution, can also be used. (See for example, E. L. Eliel, *Stereochemistry of Carbon Compounds*, McGraw Hill (1962) and [Wilen and Lochmuller, "Tables of Resolving Agents", *Journal of Chromatography* 113, 283–302 (1975)]. (−)-Zileuton may be synthesized from D-(−)-lactic acid by a procedure analogous to that of Hsiao and Kolasa [*Tet. Lett.* 33, 2969–2932 (1992)].

The magnitude of a prophylactic or therapeutic dose of (−)-zileuton in the acute or chronic management of disease will vary with the severity and nature of the condition to be treated and the route of administration. The dose and perhaps the dose frequency will also vary according to the age, body weight and response of the individual patient. In general, the total daily dose range for (−)-zileuton for the conditions described herein is from about 200 mg to about 2 g in single or divided doses. Preferably a daily dose range should be about 400 mg to about 1600 mg in single or divided doses, while most preferably a daily dose range should be about 600 mg to about 1200 mg in single or divided doses. In managing the patient, the therapy should be initiated at a lower dose, perhaps at about 400 mg to about 600 mg, and increased up to about 1200 mg or higher depending on the patient's global response. It is further recommended that children and patients over 65 years and those with impaired renal or hepatic function initially receive low doses and that they be titrated based on individual response(s) and blood level(s). It may be necessary to use dosages outside these ranges in some cases, as will be apparent to those skilled in the art. Further, it is noted that the clinician or treating physician will know how and when to interrupt, adjust, or terminate therapy in conjunction with individual patient response. The terms "an amount sufficient to alleviate asthma but insufficient to cause said adverse effects", "an amount sufficient to alleviate the symptoms of rheumatoid arthritis but insufficient to cause said adverse effects", "an amount sufficient to alleviate the symptoms of ulcerative colitis but insufficient to cause said adverse effects", "an amount sufficient to reduce atherosclerotic plaque but insufficient to cause said adverse effects" and "an amount sufficient to reduce elevated leukotriene levels but insufficient to cause said adverse effects" are encompassed by the above-described dosage amounts and dose frequency schedule.

Any suitable route of administration may be employed for providing the patient with an effective dosage of (−)-zileuton. For example, oral, pulmonary, rectal, parenteral (subcutaneous, intramuscular, intravenous), transdermal, and like forms of administration may be employed. Dosage forms include tablets, troches, dispersions, suspensions, aerosols, solutions, capsules, patches, and the like.

The pharmaceutical compositions of the present invention comprise (−)-zileuton as the active ingredient, or a pharmaceutically acceptable salt thereof, and may also contain a pharmaceutically acceptable carrier, and optionally, other therapeutic ingredients.

The terms "pharmaceutically acceptable salts" or "a pharmaceutically acceptable salt thereof" refer to salts prepared from pharmaceutically acceptable non-toxic strong bases. Since the compound of the present invention is a very weak acid, salts may be prepared from pharmaceutically acceptable non-toxic bases, particularly inorganic bases. Suitable pharmaceutically acceptable base addition salts for the compound of the present invention include metallic salts made from aluminum, calcium, lithium, magnesium, potassium, sodium and zinc. Sodium salts are particularly preferred if any salt is to be made.

The compositions of the present invention include suspensions, solutions, elixirs, aerosols, or solid dosage forms. Carriers such as starches, sugars, and microcrystalline cellulose, diluents, granulating agents, lubricants, binders, disintegrating agents, and the like are suitable in the case of oral solid preparations (such as powders, capsules, and tablets), and oral solid preparations are preferred over the oral liquid preparations.

Because of their ease of administration, tablets and capsules represent the most advantageous oral dosage unit forms, in which case solid pharmaceutical carriers are employed. If desired, tablets may be coated by standard aqueous or nonaqueous techniques.

In addition to the common dosage forms set out above, the compounds of the present invention may also be administered by controlled release means and delivery devices such as those described in U.S. Pat. Nos.: 3,845,770; 3,916,899; 3,536,809; 3,598,123; and 4,008,719, the disclosures of which are hereby incorporated by reference.

Pharmaceutical compositions of the present invention suitable for oral administration may be presented as discrete units such as capsules, cachets, tablets, or aerosol sprays, each containing a predetermined amount of the active ingredient, as a powder or granules, or as a solution or a suspension in an aqueous liquid, a non-aqueous liquid, an oil-in-water emulsion, or a water-in-oil liquid emulsion. Such compositions may be prepared by any of the methods of pharmacy, but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation.

For example, a tablet may be prepared by compression or molding, optionally, with one or more accessory ingredients. Compressed tablets may be prepared by compressing in a suitable machine the active ingredient in a free-flowing form such as powder or granules, optionally mixed with a binder, lubricant, inert diluent, surface active agent or dispersing agent. Molded tablets may be made by molding in a suitable machine, a mixture of the powdered compound moistened with an inert liquid diluent. Desirably, each tablet contains from about 200 mg to about 600 mg of the active ingredient, and each cachet or capsule contains from about 200 mg to about 600 mg of the active ingredient. Most preferably, the tablet, cachet or capsule contains either one of three dosages, about 200 mg, about 400 mg or about 600 mg of (−)-zileuton for oral administration.

The invention is further defined by reference to the following examples describing in detail the preparation of the compositions of the present invention, as well as their utility. It will be apparent to those skilled in the art that many modifications, both to materials and methods, may be practiced without departing from the purpose and interest of this invention.

The relative activity, potency and specificity of optically pure zileuton and racemic zileuton as an inhibitor of 5-lipoxygenase can be determined by a pharmacological study in vitro according to the methods of Carter et al. [*J. Pharmacol. Exp. Ther.* 256, 929–937 (1991)]. The tests provide an estimate of relative activity, potency and, through a measure of specificity, an estimate of therapeutic index.

RBL-1 cell lysate 5-lipoxygenase inhibitor potency. Adherent rat basophilic leukemia (RBL-1) cells are harvested by trypsinization, suspended (approx. $3.0 \times 10^7$ cells/mL) in buffer at pH 6.8 and lysed by sonication. The lysate is centrifuged and the supernatant-containing 5-lipoxygenase activity stored frozen until used.

Compounds are evaluated for 5-lipoxygenase inhibitory activity in incubations containing 12% RBL-1 supernatant in assay buffer at pH 6.8 using a modification of the method described by Jakschik et al. [*Biochem. Biophys. Res. Comm.* 95, 103–110 (1980)] Compounds (racemic zileuton, (+)-zileuton and (−)-zileuton) are dissolved in DMSO and preincubated with the enzyme for 20 min. at 37° C. before initiating the 5-lipoxygenase reaction by addition of arachidonic acid (AA) and [$^{14}$C]AA in aqueous $NH_4OH$ (0.028%). As an internal recovery standard, [$^3$H]-5- hydroxyeicosatetraenoic acid (HETE) is added with the substrate. Reactions are terminated after 5 min. by acidification with HCl to pH 3.5. Under these conditions, the majority of the initial product of the reaction, 5-HPETE is further converted to 5-HETE. The reducing agent triphenylphosphine (TPP) is added to convert any remaining 5-HPETE to 5-HETE.

Eicosanoids are extracted from acidified incubations using acetone and samples are prepared for TLC analysis by addition of 5-HETE and AA to permit visualization of product and substrate on TLC sheets. Aliquots of acetone extracts are applied to silica gel-impregnated glass fiber TLC sheets which are developed with hexane-ethyl acetate-glacial acetic acid (85:15:0.25). Both 5-HETE and AA are located by brief exposure to iodine vapor. The reaction product, 5-HETE can be eluted from the TLC medium and the amount of radioactivity measured using a liquid scintillation counter. Product formation in the individual incubations can then be corrected for recovery of [$^3$H]-5-HETE.

Human platelets are suspended at about $10^9$ cells/mL in assay buffer at pH 7.4. The cells are lysed by sonication, centrifuged and the supernatant containing the 12-lipoxygenase activity stored frozen until used. Compounds are evaluated for 12-lipoxygenase inhibitory activity in incubations containing 25% of the platelet supernatant and 2% DMSO in assay buffer. After 20 min. of preincubation at 37° C., reactions are initiated by adding AA, [$^{14}$C]AA in aqueous $NH_4OH$ (0.028%) and the internal recovery standard, [$^3$H]-15-HETE. Reactions are terminated after 5 min. by acidification with HCl to pH 3.5. Mass standards, 15-HETE, AA, and triphenyl phosphine (TPP) are added and the samples extracted with diethyl ether. Samples are processed essentially as described for the 5-lipoxygenase inhibition assay.

Soybean and rabbit reticulocyte 15-lipoxygenase. Compounds can be evaluated for inhibitory activity against soybean lipoxygenase, Type I (Sigma Chemical Co., St. Louis, Mo.), in incubations containing 20 U of enzyme in 10 mM sodium borate, 150 mM NaCl and 0.1% (w/v) gelatin buffer, pH 8.7. After 20 min. of preincubation with test compounds at 37° C., the reaction is initiated as before. Reactions are terminated after 5 min. by acidification with HCl to pH 3.5 and mass standards, 15-HETE, AA and TPP are added. Samples are processed essentially as described for the 5-lipoxygenase inhibition assay.

Rabbit reticulocyte lipoxygenase is partially purified using ammonium sulfate precipitation followed by CM cellulose chromatography to remove hemoglobin [Schewe et al., *Methods Enzymol.* 71, 430–441 (1981)]. Compounds are evaluated for inhibitory activity against this enzyme preparation using a procedure similar to the one used for the soybean enzyme. The assay buffer contains 0.1M potassium-phosphate and 0.05% sodium cholate adjusted to pH 7.4.

Sheep seminal vesicle microsomal cyclooxygenase. Sheep seminal vesicle microsomes are prepared using a modification of the method described by Wallach and Daniels [*Biochim. Biophys Acta* 231, 445–457 (1971)]. Test agents are combined in incubations with sheep seminal vesicle gland microsomes (2 mg/mL) and [$^{14}$C]AA in 0.125M EDTA buffer, pH 8, containing 1 mM reduced glutathione, 0.5 mM hydroquinone, 0.5 mg/mL of BSA and 2% DMSO. Reactions are terminated after 30 min at 37° C. by adding methanol followed by centrifugation. The supernatants are mixed with water-glacial acetic acid (98.3:1.7) and aspirated through $C^{18}$ Sep-Paks (Millipore) using a vacuum manifold. The columns are sequentially washed with the following mixtures of methanol-water-glacial acetic acid: 33:66:1,70:30:0.1 and 100:0:0. The major cyclooxygenase product, $PGE_2$, elutes with the 70% methanol wash. This eluant is collected directly into liquid scintillation vials and the radioactivity in the sample is measured.

Rat leukocyte 5-lipoxygenase and cyclooxygenase. Rat leukocytes are obtained from the pleural cavity of male Sprague-Dawley rats injected intrapleurally with 200 µL of a 0.05% (w/v) carrageenan solution. Contaminating erythrocytes are lysed and the cells washed and resuspended at a concentration of $2 \times 10^7$ cells/mL in Earle's balanced salts, pH 7.0, containing 20 mM 4-(2-hydroxyethyl)-1-piperazineethanesulfonic acid and 1 mg/mL of BSA. Greater than 90% of the cells should be polymorphonuclear leukocytes (PMNL) as determined by differential counting using Wright's stain.

Test compounds and DMSO vehicle (final concentration, 2%) are preincubated with the cell suspensions for 15 min at 37° C. Cellular arachidonate metabolism is initiated by adding a calcium ionophore, A23187, (final concentration, 4 µM) and terminated after 10 min by rapid cooling in an ice bath.

Samples are divided into two portions. One portion is centrifuged and the supernatant analyzed for $PGE_2$ by RIA. The other portion is extracted with methanol containing 50 ng of $PGB_2$, as an internal recovery standard. The methanolic extracts are centrifuged and aliquots of the supenatants injected onto a reversed phase $C_{18}$ column and eluted with acetonitrile (8 mM) and triethylamine formate, pH 3.5 (50:50, v\v) at a flow rate of 1 mL/min. Eluting product peaks are quantitated by UV absorbance ($LTB_4$ at 280 mm; 5-HETE at 235 mm) and are corrected for $PGB_2$ recovery. The lower limit of detection is approximately 100 pg of $LTB_4$ injected.

Human whole blood 5-lipoxygenase and cyclooxygenase. Aliquots of heparinized (20 USP U/mL) human blood (0.3 mL) from donors are preincubated with racemic zileuton, (+)-zileuton or (−)-zileuton or vehicle for 15 min at 37° C. Eicosanoid biosynthesis is initiated by adding calcium ionophore A 23187 in DMSO (final concentration, 50 µM) and terminated after 30 min by rapid cooling of the blood in an ice bath and centrifuging. The plasma is mixed with 4 volumes of methanol and allowed to stand for at least 2 hr at 3° C. before centrifuging again. The level of LTB in aliquots of the methanol-plasma extract is analyzed by RIA or by enzyme immunoassay. Similarly, cyclooxygenase activity is determined by analysis of plasma samples for thromboxane $B_2$ by enzyme immunoassay.

Rat and dog ex vivo $LTB_4$ biosynthesis. Racemic zileuton, (+)-zileuton or (−)-zileuton is suspended in 0.2% methylcellulose and administered p.o. to beagle dogs and male Sprague-Dawley rats. All animals are fasted overnight before dosing but are allowed water ad libitum. Heparinized blood samples are obtained before and at various times after compound administration in the dog study. Groups of rats are dosed with vehicle or zileuton and 1 hr and 15 min later, the animals are sacrificed and blood collected by cardiac puncture into heparized syringes. Aliquots of blood from both species are incubated at 37° C. with 50 µM with calcium ionophore, A23187. After 30 min, the blood is placed in an ice bath and analyzed for $LTB_4$ as described above.

Rat peritoneal anaphylaxis model. Rats are passively sensitized by i.p. injection of rabbit anti-BSA in PBS, pH 7.1. Three hours later the rats are injected i.p. with 4 mg of BSA in 5 mL of PBS containing 30 mM l-cysteine. Test compound or control vehicle is given by garage p.o. 1 hr before antigen challenge.

The rats are sacrificed 15 min after challenge with $CO_2$ asphyxiation, the peritoneal cavity opened and the fluid contents collected. The cavities are rinsed with 5 mL of cold phosphate buffered saline (PBS) containing 0.1% gelatin, 0.1% sodium azide, 10 mM tripotassium EDTA and 30 mM l-cysteine. The fluids are mixed with 20 mL of ice-cold methanol and then centrifuged at 1000×g for 15 min. Fluid volumes are measured and the samples stored frozen until assayed.

The incorporation of l-cysteine in the assay essentially prevents metabolic conversion of $LTD_4$ to $LTE_4$, so that the products measured are predominantly $LTC_4$ and $LTD_4$. The immunoreactive leukotriene levels in the biological samples are calculated from a $LTC_4$ standard curve.

AA-induced mouse ear edema model. Zileuton or control vehicle is given by gavage p.o. 15 min before the application of an acetone solution of 2.5% AA to both the inner and outer surfaces of one ear of male mice weighing 20 to 30 g. The opposite ears receive a like treatment of acetone vehicle. One hour later the mice are sacrificed with $CO_2$ and a section removed from the ears with a biopsy punch. These sections are weighed immediately for wet weight determinations. Edema is calculated as the percentage of increase in ear weight of the AA-treated ear compared to the contralateral acetone-treated ear.

Rat pleural reverse passive reaction. Rats are injected i.v. with 3 mg/kg of BSA in isotonic saline at 2 mL/kg. After 1 hour the rats are injected intrapleurally with approximately 1 mg of rabbit anti-BSA in 0.2 mL of isotonic saline. Zileuton or control vehicle is administered p.o. 30 min before the antibody injection. Groups of rats are sacrificed with $CO_2$ 3 hr after the intrapleural challenge. The pleural cavity is opened laterally and a phenol red dye solution containing 0.5% EDTA is dispensed into the cavity. After thorough mixing, the fluid contents are collected to assay for volume using a dye dilution technique [Carter et al., *J. Pharm. Pharmacol.* 34, 66–67 (1982)] and for white blood cell content using an electronic cell counter.

EXAMPLES

Example 1

| ORAL FORMULATION | | | |
|---|---|---|---|
| Capsules: | Quantity per capsule in mg | | |
| Formula | A | B | C |
| (−)-Zileuton | 200 | 400 | 600 |
| Lactose | 230 | 280 | 330 |
| Cornstarch | 65 | 65 | 65 |
| Magnesium Stearate | 5 | 5 | 5 |
| Compression Weight | 500 | 750 | 1000 |

The (−)-zileuton, lactose and cornstarch are blended until uniform and then the magnesium stearate is blended into the resulting powder, which is sieved and filled into suitably sized, two-piece, hard gelatin capsules using conventional machinery. Other doses may be prepared by altering the fill weight and, if necessary, changing the capsule size to suit.

Example 2

| ORAL FORMULATION | | | |
|---|---|---|---|
| Tablets: | Quantity per tablet in mg | | |
| Formula | A | B | C |
| (−)-Zileuton | 200 | 400 | 600 |
| Lactose | 205 | 245 | 245 |
| Cornstarch | 30 | 50 | 50 |
| Water (per thousand Tablets)* | 300 ml | 500 ml | 500 ml |
| Cornstarch | 60 | 100 | 100 |
| Magnesium Stearate | 5 | 5 | 5 |
| Compression Weight | 500 | 800 | 1000 |

*The water evaporates during manufacture

The (−)-zileuton is blended with the lactose until a uniform blend is formed. The smaller quantity of cornstarch is blended with the water to form the resulting corn starch paste. This is then mixed with the uniform blend until a uniform wet mass is formed. The remaining cornstarch is added to the resulting wet mass and mixed until uniform granules are obtained. The granules are then screened through a suitable milling machine, using a ¼ inch stainless steel screen. The milled granules are dried in a suitable drying oven until the desired moisture content is obtained. The dried granules are then milled through a suitable milling machine, magnesium stearate is blended in, and the resulting mixture is compressed into tablets of the desired shape, thickness, hardness and disintegration. Tablets of other strengths may be prepared by altering the ratio of active ingredient to the excipients or to the final weight of the tablet.

What is claimed is:

1. A method of treating asthma in a human which comprises administering to said human an amount of (−)-zileuton, or a pharmaceutically acceptable salt thereof, substantially free of its (+) stereoisomer, said amount being sufficient to alleviate said asthma.

2. The method of claim 1 wherein (−)-zileuton is administered by pulmonary, parenteral, transdermal, or oral administration.

3. The method of claim 2 wherein the amount of (−)-zileuton or a pharmaceutically acceptable salt thereof administered is from about 20 mg to about 2 g per day.

4. The method of claim 3 wherein the amount administered is from about 400 mg to about 1600 mg per day.

5. The method of claim 4 wherein the amount administered is from about 600 mg to about 1200 mg per day.

6. The method of claim 1 wherein the amount of (−)-zileuton or a pharmaceutically acceptable salt thereof is greater than approximately 90% by weight of the total weight of zileuton.

7. The method of claim 1 wherein the amount of said (−)-zileuton or a pharmaceutically acceptable salt thereof, substantially free of its (+) stereoisomer, is administered together with a pharmaceutically acceptable carrier.

8. A method of treating asthma in a human while substantially reducing the concomitant liability of adverse effects associated with racemic zileuton which comprises administering to a human in need of such antiasthmatic therapy an amount of (−)-zileuton, or a pharmaceutically acceptable salt thereof, substantially free of its (+) stereoisomer, said amount being sufficient to alleviate said asthma but insufficient to cause said adverse effects.

* * * * *